US010232154B2

United States Patent
O'Sullivan et al.

(10) Patent No.: US 10,232,154 B2
(45) Date of Patent: Mar. 19, 2019

(54) IMPLANTABLE MEDICAL DEVICES AND RELATED METHODS OF USE

(71) Applicant: Boston Scientific Scimed, Inc., Maple Grove, MN (US)

(72) Inventors: Conor O'Sullivan, Wilton (IE); John-Alan O'Brien, Drimoleague (IE); Frank Ryan, Frankfield (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 217 days.

(21) Appl. No.: 15/221,110

(22) Filed: Jul. 27, 2016

(65) Prior Publication Data

US 2017/0028180 A1 Feb. 2, 2017

Related U.S. Application Data

(60) Provisional application No. 62/197,971, filed on Jul. 28, 2015.

(51) Int. Cl.
*A61M 31/00* (2006.01)
(52) U.S. Cl.
CPC ... *A61M 31/002* (2013.01); *A61M 2210/1039* (2013.01)
(58) Field of Classification Search
CPC .............. A61M 31/002; A61M 25/04; A61M 2210/1039; A61B 17/1214; A61B 17/12172; A61B 17/12177
See application file for complete search history.

(56) References Cited

U.S. PATENT DOCUMENTS

| 7,361,168 | B2 * | 4/2008 | Makower | A61B 5/06 |
| | | | | 604/509 |
| 7,491,225 | B2 | 2/2009 | Weber et al. | |
| 8,007,509 | B2 | 8/2011 | Buiser et al. | |
| 8,025,635 | B2 * | 9/2011 | Eaton | A61B 17/24 |
| | | | | 604/101.01 |
| 2003/0154988 | A1 * | 8/2003 | DeVore | A61B 17/12022 |
| | | | | 128/207.15 |
| 2003/0158515 | A1 * | 8/2003 | Gonzalez | A61B 17/12022 |
| | | | | 604/93.01 |
| 2004/0034407 | A1 * | 2/2004 | Sherry | A61F 2/07 |
| | | | | 623/1.15 |
| 2007/0282425 | A1 | 12/2007 | Kleine et al. | |
| 2008/0086113 | A1 * | 4/2008 | Tenney | A61L 27/54 |
| | | | | 604/892.1 |

(Continued)

FOREIGN PATENT DOCUMENTS

EP 1 600 125 A2 11/2005

OTHER PUBLICATIONS

Lung Cancer in Chronic Obstructive Pulmonary Disease Enhancing Surgical Options and Outcomes. American Journal of Respiratory and Critical Care Medicine, vol. 138, No. 9, May 1, 2011.*

(Continued)

*Primary Examiner* — Laura A Bouchelle
(74) *Attorney, Agent, or Firm* — Bookoff McAndrews, PLLC

(57) ABSTRACT

A medical system may include an elongate member having a proximal end and a distal end, the elongate member being movable between a collapsed configuration and an expanded configuration, and a first therapeutic agent configured to treat a condition of the lung.

10 Claims, 2 Drawing Sheets

(56) References Cited

U.S. PATENT DOCUMENTS

| | | | |
|---|---|---|---|
| 2008/0221554 A1 | 9/2008 | O'Connor et al. | |
| 2009/0076623 A1* | 3/2009 | Mathis | A61B 17/12022 623/23.65 |
| 2011/0046657 A1* | 2/2011 | Guo | A61B 17/12022 606/200 |
| 2014/0275952 A1* | 9/2014 | Monroe | G06T 19/00 600/407 |

OTHER PUBLICATIONS

Babu et al., Nanoparticle-Based Drug Delivery for Therapy of Lung Cancer: Progress and Challenges, Journal of Nanomaterials, Article ID 863951, 11 pages, vol. 2013.

Chandolu et al., Treatment of Lung Cancer Using Nanoparticle Drug Delivery Systems, Current Drug Discovery Technologies, 2013, pp. 170-176, vol. 10, No. 2.

Courrier et al., Pulmonary Drug Delivery Systems: Recent Developments and Prospects, Critical Reviews in Therapeutic Drug Carrier Systems, 2002 pp. 425-498, vol. 19, Nos. 4 and 5.

Siegel et al., Cancer Statistics, 2014, CA: A Cancer Journal for Clinicians, pp. 9-29, vol. 64, No. 1.

Shaikh et al., Recent Advances in Pulmonary Drug Delivery System: A Review, International Journal of Applied Pharmaceuticals, 2010, pp. 27-31, vol. 2, Issue 4.

Montaudon et al., Assessment of bronchial wall thickness and lumen diameter in human adults using multi-detector computed tomography: comparison with theoretical models, Journal of Anatomy, Nov. 2007, pp. 579-588.

Boston Scientific, Interlock: Fibered IDC Occlusion System, 2011, 44 pages.

* cited by examiner

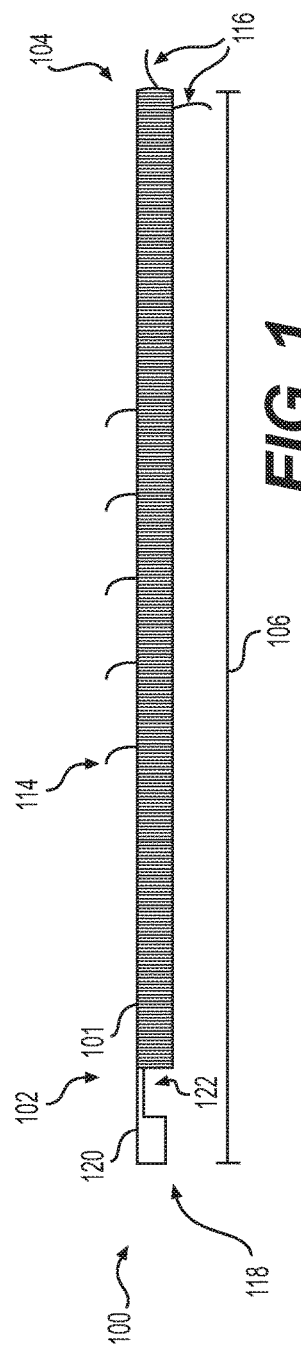
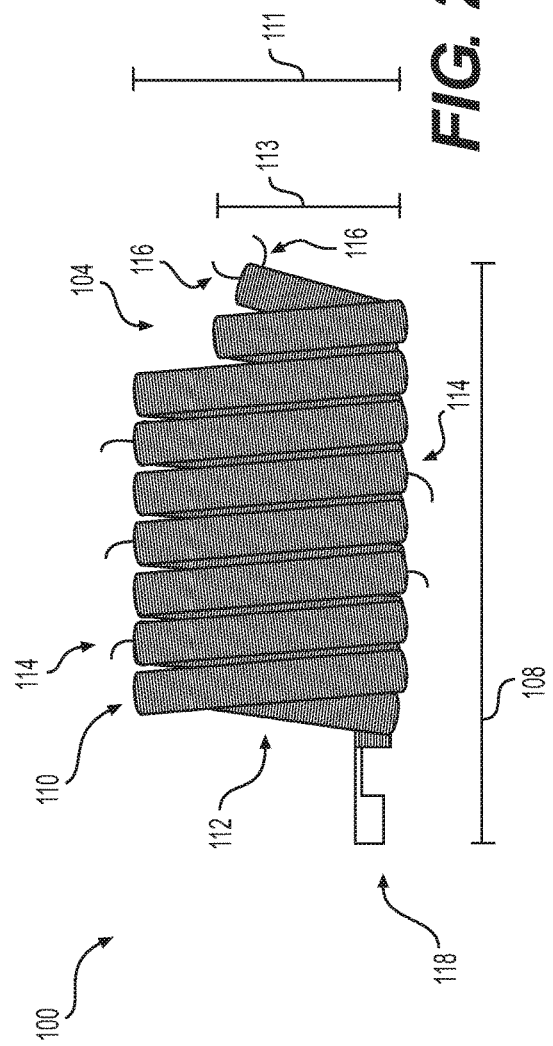
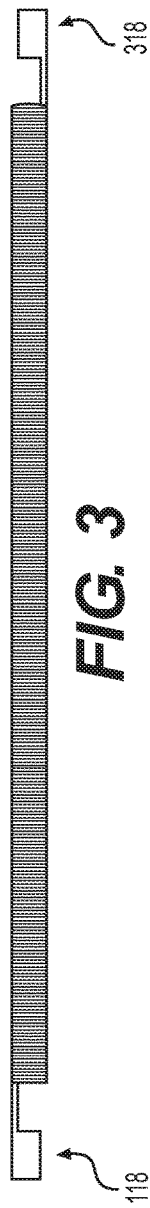
FIG. 1
FIG. 2
FIG. 3

IMPLANTABLE MEDICAL DEVICES AND RELATED METHODS OF USE

CROSS-REFERENCE TO RELATED APPLICATION(S)

This patent application claims the benefit under 35 U.S.C. § 119 to U.S. Provisional Patent Application No. 62/197,971, filed on Jul. 28, 2015, the entirety of which is incorporated herein by reference.

TECHNICAL FIELD

Examples of the present disclosure relate to implantable medical devices for delivering therapeutic agents into a body lumen, for example, a lung, and related methods of implantation and use.

BACKGROUND

In the United States, lung cancer is the second most common cancer, after prostate cancer in men, and breast cancer in women. Non-small cell lung cancers comprise the majority of lung cancers, with the remaining lung cancers being small cell lung cancers. There are few reliable mechanisms for treating lung cancer.

Chronic obstructive pulmonary disease (COPD) includes conditions such as, e.g., chronic bronchitis and emphysema. These conditions are often co-existing within patients having COPD. COPD currently affects over 15 million people in the United States alone and is currently the third leading cause of death in the country. The primary cause of COPD is inhalation of cigarette smoke, responsible for over 90% of COPD cases. The economic and social burden of the disease is substantial and is increasing. Other ailments of the lung include asthma and allergies, among others.

Chronic bronchitis is characterized by chronic cough with sputum production. Due to airway inflammation, mucus hypersecretion, airway hyperresponsiveness, and eventual fibrosis of the airway walls, significant airflow and gas exchange limitations result. Chronic bronchitis can lead to a blockage of the airways and debilitating exacerbative episodes that can pose serious health risks to COPD patients.

Emphysema is characterized by the destruction of the lung parenchyma. This destruction of the lung parenchyma leads to a loss of elastic recoil and tethering which maintains airway patency. Because bronchioles are not supported by cartilage like the larger airways, they have little intrinsic support and therefore are susceptible to collapse when destruction of tethering occurs, particularly during exhalation.

Strategies for managing COPD include smoking cessation, vaccination, rehabilitation, and drug treatments (e.g., inhalers or oral medication). Drug treatments of COPD conditions, such as, e.g., mucus production, often suffer from poor patient compliance. That is, certain patients may not accurately administer prescribed doses, reducing the efficacy of treatment. For drug treatments utilizing inhalation, there is also an accompanying drug loss due to upper airway entrapment, which may lead to an over-prescription of active drugs. For drug treatments utilizing oral administration, there is an accompanying systemic loss which also leads to an over-prescription of active drugs. The over-prescription of drugs may result in suboptimal treatment and/or a build-up of toxins within the lungs and/or other organ systems.

Thus, there remains a need for improved methods and devices for treating lung cancers and other ailments of the lungs.

SUMMARY

In one aspect, the present disclosure is directed to a medical system that may include an elongate member having a proximal end and a distal end, the elongate member being movable between a collapsed configuration and an expanded configuration, and a first therapeutic agent configured to treat a condition of the lung.

The first therapeutic agent may be configured to treat one or more of cancer, COPD, bronchitis, emphysema, asthma, and an allergy of the lung. While in the expanded configuration, the elongate member may form a coil having an outer radial surface configured to contact tissue defining a lumen of the lung. The medical system may include one or more anchoring features disposed on the outer radial surface of the coil, wherein the one or more anchoring features may be configured to pierce tissue defining the lumen. The medical system may include one or more anchoring features that extend from a distally-facing surface of the elongate member. The one or more anchoring features may be formed of a bioabsorbable material, and the elongate member may be formed from a biologically-stable material. The medical system may include a first coating on an outer radial surface of the elongate member, wherein the first coating may include the first therapeutic agent. The medical system may include a second coating on the outer radial surface of the elongate member, the second coating including a second therapeutic agent that may be different from the first therapeutic agent. The therapeutic agent may be disposed within the elongate member, and wherein an outer surface of the elongate member may be permeable to the therapeutic agent such that therapeutic agent can be delivered from within the elongate member, through the outer surface of the elongate member, and into the lumen. The elongate member may include a bioabsorbable material, and wherein the first therapeutic agent may be incorporated into the bioabsorbable material. The medical system may include a catheter and a delivery member disposed within the catheter, wherein the catheter may be configured to constrain the elongate member in the collapsed configuration, and the delivery member may be configured to interlock with the elongate member to move the elongate member through the catheter and into the lumen. The medical system may include a first interlock feature disposed at the proximal end of the elongate member, and a second interlock feature disposed at a distal end of the delivery member, wherein the first interlock feature and the second interlock feature are configured to cooperate with one another to interlock the delivery member and the elongate member. The first interlock feature may include a first flange and a first recess, and the second interlock feature may include a second flange and a second recess, wherein the first flange may be received by the second recess and the second flange may be received by the first recess when the delivery member and the elongate member are interlocked. The medical system may include a third interlock feature disposed at the distal end of the elongate member. A surface of the elongate member may include a bioadhesive.

In another aspect, the present disclosure may be directed to a method of treating a lung. The method may include inserting an elongate member into an airway of the lung via a catheter while the elongate member is in a collapsed radial configuration, and delivering the elongate member from a distal end of the catheter, wherein the elongate member may convert to an expanded radial configuration after exiting the catheter such that an outer radial surface of the elongate member contacts tissue defining the airway. The method also may include delivering a first therapeutic agent to the lung.

The first therapeutic agent may be configured to treat one or more of cancer, COPD, bronchitis, emphysema, asthma, and an allergy of the lung. The method may include interlocking a delivery member disposed within the catheter to the elongate member. The method may include releasing the elongate member from the delivery member after the elongate member exits a distal end of the catheter. The first therapeutic agent may be disposed within a lumen of the elongate member, and the first therapeutic agent may be delivered to the lung through a permeable outer surface of the elongate member. The elongate member may be formed of a bioabsorbable material, and wherein the first therapeutic agent may be delivered to the lungs as the bioabsorbable material degrades. The method may include anchoring the expandable coil in the airway wall with a bioabsorbable anchoring feature that pierces the tissue of the airway wall.

In yet another aspect, the present disclosure is directed to a method of treating lung cancer. The method may include positioning an expandable coil into an airway having a lung tumor disposed on a portion of tissue that defines the airway, and positioning the expandable coil in contact with the lung tumor. The method also may include delivering a first therapeutic agent from the expandable coil to the lung tumor to treat the lung tumor.

The method may include delivering a second therapeutic agent from the expandable coil to tissue of the lung to treat one or more of COPD, bronchitis, emphysema, asthma, and an allergy of the lung. Positioning the expandable coil into the airway may include anchoring the expandable coil in the airway wall with an anchoring feature that pierces the tissue of the airway wall.

BRIEF DESCRIPTION OF THE DRAWINGS

The accompanying drawings, which are incorporated in and constitute a part of this specification, illustrate various examples and together with the description, serve to explain the principles of the disclosed examples.

FIG. 1 is a side view of a medical device in a collapsed configuration according to an example of the present disclosure.

FIG. 2 is a side view of the medical device of FIG. 1 in an expanded configuration.

FIG. 3 is a side view of a medical device according to another example of the present disclosure.

DETAILED DESCRIPTION

Figure 4:
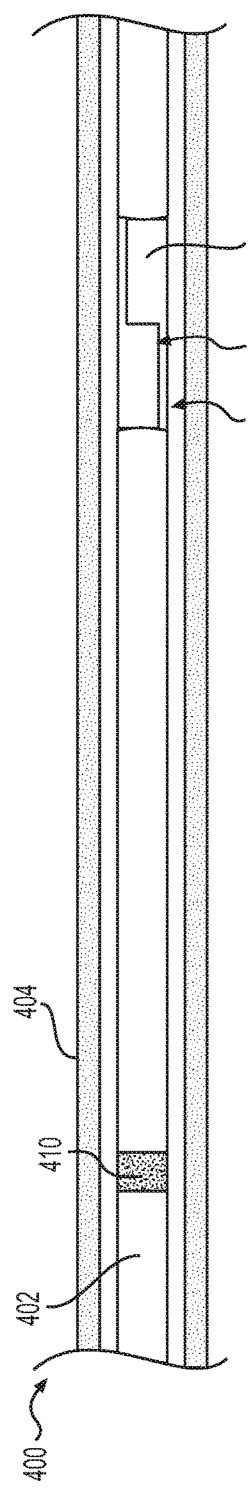
FIGS. 4 and 5 are side views of a delivery member and catheter for implanting the medical device of FIG. 1 into a body lumen, according to an example of the present disclosure.

Reference will now be made in detail to examples of the present disclosure, examples of which are illustrated in the accompanying drawings. Wherever possible, the same reference numbers will be used throughout the drawings to refer to the same or like parts or components. The term "distal" refers to the direction that is away from the user or operator and into the patient's body. By contrast, the term "proximal" refers to the direction that is closer to the user or operator and away from the patient's body.

Implantable Devices

An implantable medical device 100 is shown in FIGS. 1 and 2. Medical device 100 may be, for example, an expandable member that is movable from a collapsed configuration (FIG. 1) to an expanded configuration (FIG. 2). Medical device 100 may be configured to deliver one or more therapeutic agents to lung tissues as described in further detail below. Medical device 100 may include an elongate member 101 that extends from a proximal end 102 toward a distal end 104. In the configuration shown in FIG. 1, medical device 100 is in a collapsed radial configuration. In the collapsed radial configuration, medical device 100 may be generally straight and parallel to its longitudinal axis. Medical device 100 may have a first length 106 when disposed in the collapsed configuration.

Medical device 100 is shown in FIG. 2 in an expanded radial configuration. In the example shown in FIG. 2, medical device 100 is a coil, e.g., a helical coil having a second length 108 that is shorter than the first length 106. That is, medical device 100 may be shorter in the expanded configuration than while in the collapsed configuration due to radial expansion. In the expanded configuration, medical device 100 may have an outer radial surface 110 which may contact tissues that define a body lumen, such as, e.g., epithelium tissue that defines a lung airway. Medical device 100 may include a lumen 112 that extends longitudinally through an inner radial portion of the coil. The presence of lumen 112 may allow for normal airflow and ventilation to occur through a lung in which medical device 100 is implanted. Medical device 100 may be formed of a shape memory material, such as, e.g., Nitinol, titanium or the like, and may be heat-set and biased to the expanded coil shape. That is, when medical device 100 is unconstrained, medical device 100 may revert to the expanded configuration. While shown in FIG. 2 as a coil in the expanded radial configuration, medical device 100 may take alternative shapes. For example, medical device 100 may be a stent having one or more longitudinal and/or radial struts.

Medical device 100 may have any suitable outer diameter, such as, e.g., between 1 mm and 20 mm, depending on the size of the intended implantation site (e.g., lung airway), although other suitable diameters are also contemplated. Medical device 100 may exhibit an outward radial force that is sufficient to maintain medical device 100 in an implanted position within the lungs. The outward radial force also may be configured so as to prevent any damage or to prevent any excessive damage to tissue walls, yet also prevent the migration of medical device 100 when implanted within a body lumen. Medical devices 100 may be specifically configured to be implanted in airways having a defined range of diameters. The specific configurations may allow for a given medical device 100 to have enough radial expansion and outward radial force to contact an airway wall intended for treatment, while not having enough radial force so as to damage or excessively damage the airway wall. For example, a medical device 100 configured to be implanted into a smaller airway (e.g., a 3 mm airway) may not have a large enough diameter to be implanted into a larger airway (e.g., 15 mm). On the contrary, a medical device 100 that is configured to be implanted into the larger airway may not be suitable for implantation into a smaller airway as it may apply an excessive tissue-damaging radial force to the tissues defining the smaller airway. A medical practitioner may first determine an intended implantation site before selecting a suitable medical device 100 to implant into a patient. In one example, when medical device 100 is used to treat a lung tumor, the medical practitioner may select an implantation site for medical device 100 based on the proximity of one or more lung tumors as set forth in further detail below. In some examples, medical device 100 may have a uniform outer diameter. In other examples, different portions of medical device 100 may have different outer diameters. For example, as shown in FIG. 2, medical device 100 may have a first outer diameter 111 that is configured to contact tissue, and a second outer diameter 113 that is not configured to contact tissue. The second outer diameter 113 may be smaller than the first outer diameter 111. The portion of medical device 110 having the smaller outer diameter 113 may be distal to the portion having the first outer diameter 111. Because the second outer diameter 113 may not be configured to contact tissue, the risk of perforating the opposing vessel wall may be reduced.

The outer radial surface 110 of medical device 100 may be roughened, textured, notched, slotted, etched, sand-blasted, coated or otherwise modified to provide a better gripping surface. The outer radial surface 110 also may include features that increase the surface area of the outer radial surface to promote drug delivery into lung tissue, such as, e.g., micro-needles, micro-pores, micro-cylinders, micro-cones, micro-pyramids, micro-tubes, micro-parallel-epipeds, micro-prisms, micro-hemispheres, teeth, ribs, ridges, or the like. In some examples, the entirety of the elongate member 101, and not just outer radial surface 110, may include one or more of these features.

Medical device 100 may include one or more anchoring features, such as anchoring features 114 and 116 that are configured to help anchor medical device 100 within airway 100. The anchoring features 114 and 116 may be any suitable shape, such as, e.g., a barb, spike, or other suitable shape that is configured to pierce through tissue to prevent migration of the medical device 100 while implanted in a lung airway or other body lumen. Anchoring features 114 and 116 may extend radially outward from outer radial surface 110, and may be both longitudinally and radially staggered from one another. Anchoring features 114 and 116 may be substantially similar to one another, except that anchoring features 116 may be disposed at the distal end 104 of medical device 100. Some anchoring features 116 may extend from outer radial surface 110, while other anchoring features 116 may extend from a distally-facing surface at distal end 104 of medical device 100. The anchoring features 116 may be configured to anchor the distal end 104 as medical device 100 is ejected from a catheter as set forth below. That is, anchoring features 116 may be configured to pierce through tissue and anchor distal end 104 within the lung airway while a remainder of medical device 100 is still disposed within the catheter.

In addition to, or as an alternative to anchoring features 114 and 116, the outer radial surface 110 may be coated with a bioadhesive to help anchor medical device 100 within a body lumen. In some examples, the bioadhesive material(s) may include, but are not limited to, amino adhesives, adhesive surface proteins (MSCRAMMS), adhesively modified biodegradable polymers such as Fatty Ester Modified PLA/PLGA, polymer materials, minigel particles, or other suitable bioadhesives. The bioadhesive material may be dissolved in a solvent or co-solvent blend prior to application to the outer radial surface 110. The solvent may include alcohols (e.g., methanol, ethanol, and isopropanol), water, or another suitable solvent.

Amino acid bioadhesives may be utilized to facilitate adhesion of outer radial surface 110 to a target location. Zwitterionic amino acids may be employed as a layer or as a component of outer radial surface 110. In one embodiment, the amino acid 3,4-L-dihydroxyphenylalanine (DOPA), which is a tyrosine derivative found in high concentrations in the "glue" proteins of mussels, may be utilized.

MSCRAMMs (microbial surface components recognizing adhesive matrix molecules) may be employed as a bioadhesive. MSCRAMMS may include materials naturally-produced by pathogens to initiate adhesion to the host extracellular matrix to initiate infection. These adhesive surface proteins may be isolated or synthesized, and utilized to facilitate adhesion of medical device 100 within a body lumen.

Adhesively modified biodegradable polymers may include DOPA (L-3,4-dihydroxyphenylalanine) modified PLA (polylactic acid), PLGA poly(lactide-co-glycolide), among others. In such embodiments, examples of suitable adhesive moieties include, but are not limited to, mono-palmitate, monostearin, glycerol, dilaurin, iso-stearyl alcohol, or the like.

Other polymer materials may alternatively be utilized as bioadhesives, including, but not limited to, proteins (e.g., gelatin) and carbohydrates (e.g., starch). For example, polysaccharides such as sorbitol, sucrose, xylitol, anionic hydrated polysaccharides (gellan, curdlan, XM-6, and xanthan) may also be employed as a bioadhesive. Other suitable materials include derivatives of natural compositions such as algenic acid, hydrated gels and the like, and also biocompatible polymers and oligomers such as dextrans, dextranes, dextrins, hydrogels including, but not limited to, polyethylene glycol (PEG), polyethylene glycol/dextran aldehyde, polyethylene oxide, polypropyline oxide, polyvinylpyrrolidine, polyvinyl acetate, polyhydroxyethyl methacrylate, and polyvinyl alcohol, as well as derivatives thereof may also be employed herein.

Minigel particles may additionally or alternatively be utilized as a bioadhesive. One exemplary bioadhesive is poly(NIPAM) (poly(N-isopropylacrylamide)) minigel particles. Poly(NIPAM) may be in a liquid state at room temperature, and an adhesive at body temperature. Additionally, for improved retention of the polymer on outer radial surface 110, minigel particles may be crosslinked or mixed with a higher molecular weight polymer to allow enough time for retention of the minigel to the medical device during delivery, or uncrosslinked minigel particles can be employed in a crosslinked polymer network.

Medical device 100 also may include a first interlock feature 118. Interlock feature 118 may include an interior passageway (not shown) that extends longitudinally through the interlock feature 118 to allow a control wire (not shown) to pass through the interlock feature 118. Interlock feature 118 may include a flange 120, and a recess 122 that is adjacent to flange 120. Flange 120 and recess 122 may be configured to interlock with a similarly-shaped flange and recess of another interlock feature 318 or 418, as discussed further below with reference to FIGS. 3-5.

As shown in FIG. 3, medical device 100 is shown with a second interlock feature 318 disposed at distal end 104. The second interlock feature 318 may be substantially similar to first interlock feature 118, and may be configured to interact with interlock features disposed on either a delivery member 402 (shown in FIGS. 4 and 5), or on an adjacent medical device 100 (shown in FIG. 3). The presence of the second interlock feature 318 may allow a plurality of medical devices 100 to be inserted into a patient using the same delivery member 402 and catheter 404 during the same procedure without withdrawing the catheter 404 from the lungs.

The outer radial surface 112 of medical device 100 may be coated with a coating containing one or more therapeutic agents for delivery into lung tissue. The coating may be a polymer coating applied to the outer surfaces of medical device 100. In some examples, the polymer coating may be a styrene-isobutylene based block copolymer, olefin polymer, polyethylene, polypropylene, polyvinyl chloride, polytetrafluoroethylene, fluorinated ethylene propylene copolymer, polyvinyl acetate, polystyrene, poly(ethylene teraphthalate), polyurethane, polyurea, silicone rubbers, polyam ides, polycarbonates, polyaldehydes, natural rubbers, polyester copolymers, styrene-butadiene copolymers ethylene vinyl acetate, polyorthoesters, polyiminocarbonates, aliphatic polycarbonates, polycaprolactone (PCL), poly-DL-lactic acid (DL-PLA) or poly-L-lactic acid (L-PLA), lactide, polyphosphazenes, polyethylene oxide or polyethylene terephthalate (PET), polybutylene terephthalate(PBT), PEBAX, Nylon, or polycaprolactone, polyorthoesters, polylactic acids, polyglycolic acids, albumin or combinations of any of the above. The coating also may include any other suitable material.

In some examples, medical device 100 may include multiple coatings. In one example, medical device 100 may include multiple coatings that cover different surfaces of the medical device 100 such that the multiple coatings are simultaneously in contact with tissues of the lung. For example, a first coating containing an anti-cancer agent may be disposed on a first portion of the outer radial surface 110, while a second coating containing a steroid, cough suppressant, or a different anti-cancer agent, may be disposed on a second portion of the outer radial surface 110 that is adjacent to the first portion. Thus, the first and second coatings each may distribute different therapeutic agents to tissues of the lung at the same time.

In another example, coatings may be layered on one another. For example, a first coating having a first therapeutic agent may be layered directly on the surface of the medical device, while a second coating having a second therapeutic agent different from the first therapeutic agent, may be layered onto the first coating. After initial implantation of medical device, only the second therapeutic agent may be delivered into tissues of the lung. However, the second coating may degrade and/or the second therapeutic agent may be depleted over time, at which point, the first therapeutic agent may be delivered into tissues of the lung. This layering of coatings may allow for more tailored treatment regimens utilizing implantable medical device 100. For example, some patients may benefit from a first treatment regime over a first period of time, e.g., one day to one or more years, yet may benefit from a different treatment regime over a second and subsequent period of time. It is further contemplated that the different coatings may include one or more of the same therapeutic agents, but may either add therapeutic agents, remove agents, and/or alter the concentrations of different therapeutic agents based on anticipated therapeutic needs.

In an alternative example, some or all of medical device 100 may be formed from a bioabsorbable material. According to one example, at least one portion of medical device 100 may include one or more commercially available grades of polylactide, poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester, poly(amino acids), poly(alpha-hydroxy acid), collagen or other connective proteins or natural materials, polycaprolactone, and copolymers of these materials as well as composites thereof and combinations of other biodegradable polymers.

In one example, the entirety of medical device 100 (including elongate member 101 and anchoring features 114 and 116) may be formed of a bioabsorbable material. One or more therapeutic agents may be incorporated into the bioabsorbable material forming the medical device 100, and those therapeutic agents may be introduced into the body as the medical device 100 is degraded. Thus, the rate at which therapeutic agents disposed within the bioabsorbable materials are released into the body may be controlled by the rate of degradation of the bioabsorbable materials.

In another example, only anchoring features 114 and 116 may be formed of a bioabsorbable material, while a remainder of the medical device 100 is formed from a non-bioabsorbable, or otherwise biologically-stable material. In these examples, the bioabsorbable anchoring features 114 and 116 may prevent migration of an implanted device after implantation. However, if treatment is only desired for a finite period of time, a medical practitioner may remove the medical device 100 in a subsequent procedure. When the anchoring features 114 and 116 are bioabsorbable, they may degrade prior to removal of the medical device 100, potentially reducing the amount of damage to airway walls when the medical device 100 is removed. When the anchoring features 114 and 116 are formed from non-bioabsorbable materials, removing a medical device 100 having anchor features embedded into the tissue may cause damage to the tissue (e.g., tearing and puncturing of the tissue).

In another example, medical device 100 may include one or more lumens (not shown) extending through an interior of the elongate member 101, and having one or more therapeutic agents flowing through the lumens. In these examples, the outer radial surface 110 may be formed of a membrane that forms an exchange interface with lung tissues. The membranes may be configured to allow for the transfer of therapeutic agent disposed in the lumens of medical device 100 into lung tissue. The membranes may include microfibers or microtubes (e.g., formed by electrospinning among other techniques) to increase exchange surface areas. The membrane may have relatively high membrane areas and thin walls, contributing to a relatively large surface area and greater delivery rates for the size of the device. The therapeutic agent may be disposed in a fluid flowing through the lumens.

In one example, a substantial entirety of first elongate member 101 may define a lumen, e.g., when elongate member 101 is a coil depicted in FIG. 2. When elongate member 101 is a stent, one or more of the struts of the stent each may define one or more lumens. Alternatively, outer radial surface 110 may include one or more holes or conduits in fluid communication with the lumens. In such examples, therapeutic agent flowing through the lumens can exit medical device 100 via the holes or conduits, and may enter the lungs. The medical device 100 may be refillable via one or more conduits (not shown) in a subsequent procedure. The fluid flowing through the lumens may be actively pumped (e.g., by a micropump), or the natural movement of the lungs during inhalation and exhalation may be sufficient to drive fluid flow and the delivery of therapeutic agent from medical device 100 to lung tissue.

Therapeutic Agents

In some examples, the support members of the present disclosure may be coated with one or more of the following therapeutic agents, such as, e.g., anti-cancer agents, cough suppressants, steroids, or drugs to treat various symptoms of reversible or chronic obstructive pulmonary disease. The precise mixture and concentrations of agents utilized with medical device 100 may be specifically tailored to the symptoms and disease states of a given patient. When multiple medical devices 100 are implanted in a patient, the different medical devices 100 may have different mixtures and/or concentrations of therapeutic agents.

Therapeutic agents may be selected to treat cancers of the lung that invade the bronchi or arise from bronchial epithelium. In one example, the targeted cancer may be adenocarcinoma which arise from the bronchial mucosal glands, and occur in a peripheral location (e.g., parenchyma) within the lung. In some examples, the targeted cancer may be formed at the site of pre-existing scars, wounds, or inflammation (e.g., a scar carcinoma), or otherwise along the lung epithelium. In another example, the targeted cancer may be bronchoalveolar carcinoma, which is a distinct subtype of adenocarcinoma with a manifestation as an interstitial lung disease on a chest radiograph. Bronchoalveolar carcinoma may arise from type II pneumocytes, and may grow along alveolar septa as a solitary peripheral nodule, multifocal disease, or a rapidly progressing pneumonic form. In another example, the target cancer may be squamous cell carcinoma (SCC), which may be found in the central parts of the lung (e.g., hilar structures). Squamous cell carcinoma may manifest as a cavitary lesion in a proximal bronchus. In another example, peripheral, large-cell carcinomas may be targeted. In yet another example, small cell lung carcinoma (SCLC) arising in bronchial locations and infiltrating the bronchial submucosa may be targeted by one or more therapeutic agents of the present disclosure.

Exemplary therapeutic agents that may help prevent excessive cell growth may include Paclitaxel, and various olimus drugs (everolimus, sirolimus). The term "therapeutic agent" as used in the present disclosure may encompass therapeutic agents, genetic materials, and biological materials and can be used interchangeably with "biologically active material." In one example, the therapeutic agent may be an anti-cell proliferation (restenotic) agent. In other examples, the therapeutic agent may inhibit smooth muscle contraction, migration or hyperactivity, mucus production and mucus thickening. Non-limiting examples of suitable therapeutic agent may include heparin, heparin derivatives, clotting or haemostatic agents to stem acute bleeding from device implantation, urokinase, dextrophenylalanine proline arginine chloromethylketone (PPack), enoxaprin, angiopeptin, hirudin, acetylsalicylic acid, tacrolimus, zotarolimus, pimecrolimus, amlodipine, doxazosin, glucocorticoids, betamethasone, dexamethasone, prednisolone, corticosterone, budesonide, sulfasalazine, rosiglitazone, mycophenolic acid, mesalamine, 5-fluorouracil, cisplatin, vinblastine, vincristine, epothilones, methotrexate, azathioprine, adriamycin, mutamycin, endostatin, angiostatin, thymidine kinase inhibitors, cladribine, lidocaine, bupivacaine, ropivacaine, D-Phe-Pro-Arg chloromethyl ketone, trapidil, liprostin, tick antiplatelet peptides, vascular endothelial growth factors, growth factor receptors, transcriptional activators, translational promoters, antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin, vasodilating agents, agents which interfere with endogenous vasoactive mechanisms, antioxidants, probucol, antibiotic agents, penicillin, cefoxitin, oxacillin, tobramycin, angiogenic substances, fibroblast growth factors, estrogen, estradiol (E2), estriol (E3), 17-beta estradiol, digoxin, beta blockers, captopril, enalopril, statins, steroids, vitamins (e.g., vitamin A may have lung repair properties), 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, 2'-O-ester with N-(dimethylaminoethyl) glutamide hydrochloride salt, nitroglycerin, nitrous oxides, nitric oxides, digitalis, and glycosides. In one example, the therapeutic agent may be a smooth muscle cell inhibitor or antibiotic. In yet another example, the therapeutic agent may be an antibiotic such as erythromycin, amphotericin, rapamycin, or the like.

Genetic materials may include DNA or RNA, including, such as, e.g., DNA/RNA encoding a useful protein stated below, intended to be inserted into a human body, including viral vectors and non-viral vectors.

Biological materials may include cells, yeasts, bacteria, proteins, peptides, cytokines and hormones. Examples of peptides and proteins may include vascular endothelial growth factor (VEGF), transforming growth factor (TGF), fibroblast growth factor (FGF), epidermal growth factor (EGF), cartilage growth factor (CGF), nerve growth factor (NGF), keratinocyte growth factor (KGF), skeletal growth factor (SGF), osteoblast-derived growth factor (BDGF), hepatocyte growth factor (HGF), insulin-like growth factor (IGF), cytokine growth factors (CGF), platelet-derived growth factor (PDGF), hypoxia inducible factor-1 (HIF-1), stem cell derived factor (SDF), stem cell factor (SCF), endothelial cell growth supplement (ECGS), granulocyte macrophage colony stimulating factor (GM-CSF), growth differentiation factor (GDF), integrin modulating factor (IMF), calmodulin (CaM), thymidine kinase (TK), tumor necrosis factor (TNF), growth hormone (GH), bone morphogenic protein (BMP) (e.g., BMP-2, BMP-3, BMP-4, BMP-5, BMP-6 (Vgr-1), BMP-7 (PO-1), BMP-8, BMP-9, BMP-10, BMP-11, BMP-12, BMP-14, BMP-15, BMP-16, etc.), matrix metalloproteinase (MMP), tissue inhibitor of matrix metalloproteinase (TIMP), cytokines, interleukin (e.g., IL-1, IL-2, IL-3, IL-4, IL-5, IL-6, IL-7, IL-8, IL-9, IL-10, IL-11, IL-12, IL-15, etc.), lymphokines, interferon, integrin, collagen (all types), elastin, fibrillins, fibronectin, vitronectin, laminin, glycosaminoglycans, proteoglycans, transferrin, cytotactin, cell binding domains (e.g., RGD), and tenascin. In some examples, BMP's may be BMP-2, BMP-3, BMP-4, BMP-5, BMP-6, BMP-7. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. Delivery media can be formulated as needed to maintain cell function and viability. Cells may include progenitor cells (e.g., endothelial progenitor cells), stem cells (e.g., mesenchymal, hematopoietic, neuronal), stromal cells, parenchymal cells, undifferentiated cells, fibroblasts, macrophage, and satellite cells.

Other non-genetic therapeutic agents may include: antithrombogenic agents; anti-proliferative agents, or monoclonal antibodies capable of blocking smooth muscle cell proliferation; antithrombin compounds, platelet receptor antagonists, anti-thrombin antibodies, anti-platelet receptor antibodies, aspirin (aspirin is also classified as an analgesic, antipyretic and anti-inflammatory therapeutic agent), DNA demethylating therapeutic agents such as 5-azacytidine, which is also categorized as a RNA or DNA metabolite that inhibit cell growth and induce apoptosis in certain cancer cells; vascular cell growth promoters such as growth factors, growth factor receptors, transcriptional activators, and translational promoters; vascular cell growth inhibitors such as anti-proliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents, and agents which interfere with antibiotic agents, such as tobranycin; therapeutic agents for heart failure; and macrolides. Biological materials may include anti-proliferative therapeutic agents such as restenosis-inhibiting agents. In some examples, restenosis-inhibiting agents may include microtubule stabilizing agents.

Other suitable therapeutic agents may include halofuginone; inhibitors of HSP90 heat shock proteins such as geldanamycin; microtubule stabilizing agents such as epothilone D; phosphodiesterase inhibitors such as cliostazole; Barkct inhibitors; phospholamban inhibitors; and Serca 2 gene/proteins.

In some examples, the therapeutic agent may be capable of altering the cellular metabolism or inhibiting a cell activity, such as protein synthesis, DNA synthesis, spindle fiber formation, cellular proliferation, cell migration, microtubule formation, microfilament formation, extracellular matrix synthesis, extracellular matrix secretion, or increase in cell volume. In other examples, the therapeutic agent may be capable of inhibiting cell proliferation and/or migration.

One or more therapeutic agents also may be selected from the family of oral or inhaled medications currently available for treatment of COPD, asthma, or other conditions of the lung. Additionally, therapeutic agents may be used to treat any other condition of the body. In one example, the therapeutic agent may include a vaccine (e.g., a flu vaccine) to be delivered over a period of multiple months (e.g., the winter season) to a patient. In some examples, the therapeutic agent may include bronchodilators, inhaled steroids, oral steroids, phosphodiesterase-4 inhibitors (e.g., roflumilast), theophylline, or any suitable combination. Bronchodilators, which may otherwise be delivered by inhalation, may include long-acting bronchodilators (tiotropium, salmeterol, formoterol, arformoterol, indacaterol, aclidinium, and the like) or short-acting bronchodilators (albuterol, levalbuterol, ipratropium, and the like). Inhaled steroids may include inhaled corticosteroids that may reduce airway inflammation and help prevent exacerbations (fluticasone, budesonide, and the like). Exemplary combinations of drugs include salmeterol and fluticasone, and formoterol and budesonide. Other therapeutic agents, such as, e.g., carbocisteine, mecysteine, N-acetylcysteine, may be additionally or alternatively utilized.

In certain examples, the therapeutic agents for use in the medical devices of the present disclosure can be synthesized by methods well known to one skilled in the art.

The release profile of a therapeutic agent from different surfaces of a medical device 100 may vary. In one example, one or more therapeutic agent(s) may be released from different surfaces of medical device 100 at different release rates (e.g., amount released per time unit), different times of release (e.g., starting/ending time of release or duration of release), and/or different amounts released. For example, in one example, a therapeutic agent may be released from a first portion of outer radial surface 110 at a different (e.g., higher or lower) rate, a different (e.g., earlier or later) starting/ending time, a different (e.g., longer or shorter) duration, and/or a different (e.g., greater or less) amount than the rate, starting time, duration, and/or amount at which said therapeutic agent and/or other therapeutic agent(s) are being released from a different portion of the coil. There can also be time delays between the release of therapeutic agents from different surfaces of the outer radial surface 110.

The release profiles of the therapeutic agent(s) from different surfaces of the medical device 100 may be adjusted based on a variety of factors, such as the therapeutic agents being used and the desired therapeutic effects to be achieved. For example, the physiochemical properties of (1) the therapeutic agent(s) (e.g., particle size, shape, mass, or nature) and the polymer(s) of the coating compositions, (2) the solvent(s) used to prepare the coating compositions, (3) the process with which the coating compositions are coated onto the surfaces of the medical device, or a combination thereof, can be modified based on knowledge in the art.

Delivery System

Figure 5:
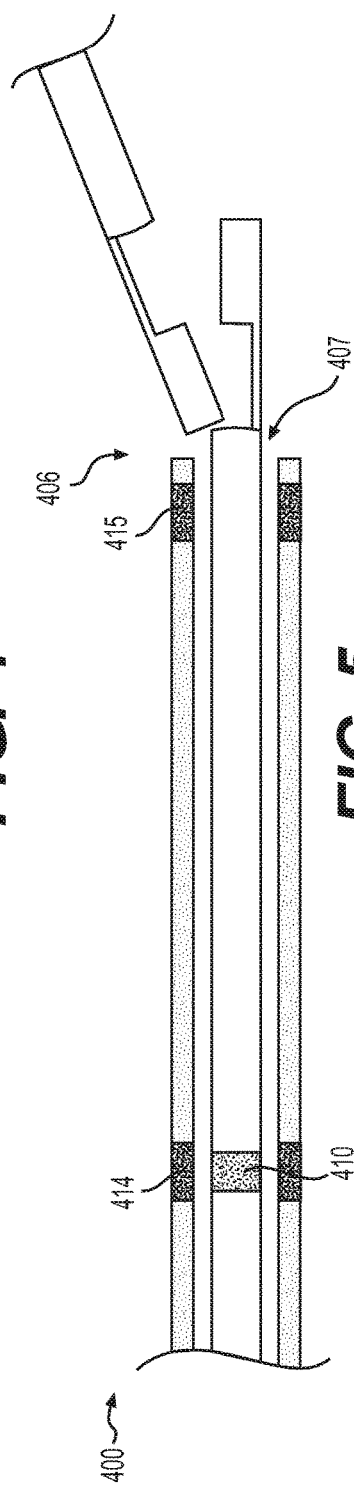

FIG. 4 depicts an example delivery system 400 that may be used to deliver a medical device 100 to a body lumen, e.g., a lung airway. Delivery system 400 may include delivery member 402 (e.g., a wire) disposed within a catheter 404. Delivery member 402 may include a positioning marker 410 disposed at a distal end of delivery member 402. Catheter 404 also may include a positioning marker 414 that is proximal to opening 407 at distal end 406 of the catheter 404. Catheter 404 also may include a positioning marker 415 disposed at distal end 406. Positioning markers 410, 414, and 415 may be radiopaque markers that can be visualized by visualization techniques, such as, e.g., fluoroscopy. The positioning markers may be formed from any suitable radiopaque material such as, e.g., gold, platinum, tantalum, tungsten, iridium, and ruthenium. The distance between positioning marker 410 and interlocking feature 418 (e.g., the distal end of delivery member 402) may be greater than the distance between positioning marker 414 and opening 407 (e.g., the distal end 406 of catheter 404). Thus, when positioning marker 410 of delivery member 402 is longitudinally aligned with positioning marker 414 of catheter 404 (as shown in FIG. 5), an entirety of medical device 100 may be disposed outside of catheter 404, interlocking feature 418 of delivery member 402 may be disposed within the body lumen, and the interlocking feature 418 may disengage from interlocking feature 118 of medical device 100.

Delivery member 402 may be movable relative to catheter 404 to deliver one or more medical devices 100 from the opening 407 (e.g., a distally-facing opening) disposed at distal end 406 of catheter 404. In some examples, a distally directed force may be applied to delivery member 402 to direct one or more medical devices 100 from opening 407. Alternatively, catheter 404 may be retracted relative to delivery member 402 to deliver medical devices 100 to a body lumen.

Catheter 404 may include a locking mechanism (not shown) that is configured to maintain the position of catheter 404 relative to delivery member 402. That is, when engaged, the locking mechanism may prevent the movement of delivery member 402 through a lumen of catheter 404. The locking mechanism may be a narrowed section of catheter 404, whereby catheter 404 may gradually reduce in size (lumen diameter) to the locking mechanism. The locking mechanism may be sized to hold delivery member 402 via, e.g., a friction fit. Such contact may be, for example, a friction fit which applies force to the delivery member 402 to hold it in place. The locking mechanism may be sized so that a particular amount of force applied to the delivery member 402 or the catheter 404 may overcome the effect of the friction fit to allow the delivery member 402 to slide relative to the catheter 404. In another example, the locking mechanism may be a portion of the catheter 404 that has been twisted under heat to deform and grip the delivery member 402. In this example, the locking mechanism can be unlocked, e.g., by untwisting the catheter 404, to allow the delivery member to move freely.

Delivery member 402 also may include an interlock feature 418 having a flange 420 and a recess 422. Interlock feature 418 may be substantially similar to interlock feature 118 described with reference to FIG. 1. With reference to both FIGS. 1 and 4, the flange 120 of first interlock feature 118 may cooperate with recess 422 of interlock feature 418, while the recess 122 of the first interlock feature 118 may receive a flange 420 of the interlock feature 418. When interlock features 118 and 418 are coupled to one another, delivery member 402 may be used to advance medical device 100 through catheter 404 and into the body.

Figure 6:
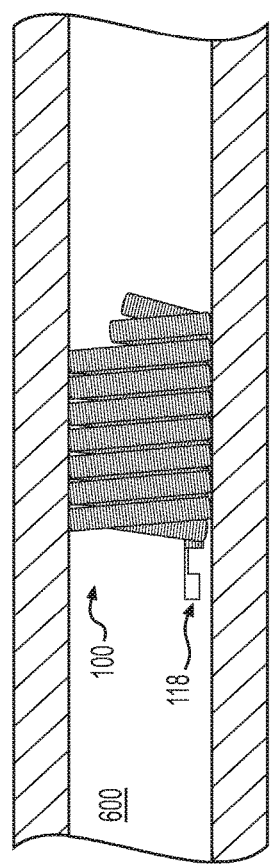
FIG. 6 is an illustrative view of the medical device of FIG. 1 implanted into a body lumen, according to an example of the present disclosure.

The medical device 100 may be inserted into the lung airway of a patient, under anaesthesia (e.g., local anaesthesia), by passing the catheter 404 (with a delivery member 402 interlocked to a medical device 100 constrained in the catheter) through the nose or mouth of the patient through a bronchoscope (or similar device) and into the lungs. The procedure may be visualized via, e.g., fluoroscopy. Catheter 400 may be advanced to a desired treatment site by positioning marker 415 at or adjacent to the treatment site. Then, once positioned at the desired treatment or implantation location, a medical practitioner may apply a distally-directed force to delivery member 402, forcing medical device 100 distally outward from the opening 407 of catheter 404. The medical practitioner may advance delivery member 402 until positioning markers 410 and 414 are aligned in the same or similar longitudinal locations. Once positioning markers 410 and 414 are aligned, the entirety of medical device 100 may be disposed within the body lumen and outside of catheter 404. Further, interlock feature 418 of delivery member 402 also may be disposed outside of the catheter 404 such that catheter 404 no longer constrains the interlock, allowing medical device 100 to separate from delivery member 402. Delivery member 402 and catheter 404 can either be entirely withdrawn from the lungs, or may be positioned elsewhere to deliver additional medical devices to different treatment locations. FIG. 6 shows a medical device 100 implanted within a body lumen 600.

Although the examples described above have been disclosed in connection with medical devices for insertion into a lung system, those skilled in the art will understand that the medical devices set out above can be implemented in any suitable body lumen (e.g., blood vessels, the biliary tract, gastrointestinal lumens, and the like) without departing from the scope of the disclosure as defined by the claims. In particular, constructional details, including manufacturing techniques and materials, are well within the understanding of those of skill in the art and have not been set out in any detail here. These and other modifications and variations are well within the scope of the present disclosure and can be envisioned and implemented by those of skill in the art.

Other examples of the present disclosure will be apparent to those skilled in the art from consideration of the specification and practice of the examples disclosed herein. It is intended that the specification and examples be considered as exemplary only, and departures in form and detail may be made without departing from the scope and spirit of the present disclosure as defined by the following claims.

What is claimed is:

1. A method of treating a lung, the method including:
   determining a size of an airway of the lung;
   selecting a size of a first member to be inserted into the airway of the lung based on the size of the airway, to prevent damage to the airway;
   inserting the first member into the airway of the lung via a catheter while the first member is in a collapsed radial configuration;
   delivering the first member from a distal end of the catheter, wherein the first member converts to an expanded radial configuration after exiting the catheter such that an outer radial surface of the first member contacts tissue defining the airway; and
   delivering a first therapeutic agent to the lung;
   wherein, while in the expanded radial configuration, the first member forms a coil with a first portion and a distalmost portion, the first portion having a first outer diameter, and the distalmost portion having a second outer diameter that is less the first outer diameter.

2. The method of claim 1, wherein the first therapeutic agent is configured to treat COPD and asthma.

3. The method of claim 1, further including interlocking a delivery member disposed within the catheter to the first member.

4. The method of claim 3, further including releasing the first member from the delivery member after the first member exits the distal end of the catheter.

5. The method of claim 1, wherein the first therapeutic agent is disposed within a lumen of the first member, the outer radial surface of the first member is permeable, and the first therapeutic agent is delivered to the lung through the permeable outer radial surface of the first member.

6. The method of claim 1, wherein the coil is an expandable coil, and the method further includes anchoring the expandable coil in the airway wall with a bioabsorbable anchoring feature that pierces the tissue of the airway wall.

7. The method of claim 1, wherein the distalmost portion does not contact tissue when the coil is at rest in the airway.

8. The method of claim 7, wherein the first therapeutic agent includes a bronchodilator.

9. The method of claim 8, further including delivering a second therapeutic agent from the coil, wherein the second therapeutic agent includes a steroid configured to reduce airway inflammation.

10. The method of claim 9, wherein the bronchodilator includes one or more of albuterol, levalbuterol, and ipratropium, and the steroid includes one or more of fluticasone and budesonide.

* * * * *